US012146149B2

(12) United States Patent
Hagner McWhirter et al.

(10) Patent No.: US 12,146,149 B2
(45) Date of Patent: Nov. 19, 2024

(54) METHOD FOR ADENOVIRUS PURIFICATION

(71) Applicant: Cytiva BioProcess R&D AB, Uppsala (SE)

(72) Inventors: Asa Hagner McWhirter, Uppsala (SE); Anna Akerblom, Uppsala (SE)

(73) Assignee: Cytiva BioProcess R&D AB, Uppsala (SE)

( * ) Notice: Subject to any disclaimer, the term of this patent is extended or adjusted under 35 U.S.C. 154(b) by 475 days.

(21) Appl. No.: 17/047,843

(22) PCT Filed: Apr. 24, 2019

(86) PCT No.: PCT/EP2019/060431
§ 371 (c)(1),
(2) Date: Oct. 15, 2020

(87) PCT Pub. No.: WO2019/206940
PCT Pub. Date: Oct. 31, 2019

(65) Prior Publication Data
US 2021/0292788 A1    Sep. 23, 2021

(30) Foreign Application Priority Data
Apr. 25, 2018  (GB) ..................... 1806736

(51) Int. Cl.
*C12N 15/86*   (2006.01)
*C12N 7/00*    (2006.01)
*C12N 15/861*  (2006.01)

(52) U.S. Cl.
CPC ............... *C12N 15/86* (2013.01); *C12N 7/00* (2013.01); *C12N 15/861* (2013.01); *C12N 2710/10043* (2013.01); *C12N 2710/10051* (2013.01)

(58) Field of Classification Search
CPC ............ C12N 15/86; C12N 7/00; C12N 2710/10051; C12N 15/861; C12N 2710/10151
See application file for complete search history.

(56) References Cited

U.S. PATENT DOCUMENTS

| | | | | |
|---|---|---|---|---|
| 9,687,564 | B2 * | 6/2017 | Pearlman | ............ A61K 48/0091 |
| 10,493,380 | B2 * | 12/2019 | Bergstrom | ............. C07K 16/00 |
| 2012/0201784 | A1 | 8/2012 | Pearlman et al. | |
| 2017/0002332 | A1 | 1/2017 | Boudeffa et al. | |
| 2017/0050121 | A1 | 2/2017 | Bergstrom | |

FOREIGN PATENT DOCUMENTS

| | | |
|---|---|---|
| CN | 101155915 A | 4/2008 |
| JP | 2017503486 A | 2/2017 |
| WO | 9627677 A2 | 9/1996 |
| WO | WO-9954441 A1 * 10/1999 | ........... B01D 15/363 |
| WO | 2006108707 A1 | 10/2006 |
| WO | 2017/019432 A1 | 2/2017 |

OTHER PUBLICATIONS

Shen et al. Optimization and scale-up of cell culture and purification processes for production of an adenovirus-vectored tuberculosis vaccine candidate. Vaccine. Jun. 17, 2016;34(29):3381-7. (listed in IDS). (Year: 2016).*
GE Healthcare Bio-Sciences AB (Capto Core 700 in vaccine processing, 29-1433-49 AA Mar. 2015). (https://cdn.cytivalifesciences.com/api/public/content/digi-17547-original). (Year: 2015).*
Riske F, Berard N, Albee K, Pan P, Henderson M, Adams K, Godwin S, Spear S. Development of a platform process for adenovirus purification that removes human SET and nucleolin and provides high purity vector for gene delivery. Biotechnol Bioeng. Mar. 2013; 110(3):848-56. (Year: 2013).*
U.S. Pharmacopeia National Formulary 2016 (Year: 2016).*
ATCC-VR-1516—Adenovirus Type 5 Reference Material-Product Information Sheet—2010 (Year: 2010).*
PCT International Search Report and Written Opinion for PCT/EP2019/060431 mailed Jun. 7, 2019 (17 pages).
Great Britain Search Report for GB 1806736.3 mailed Jan. 16, 2019 (6 pages).
Appaiahgari et al., "Adenoviruses as Gene/Vaccine Delivery Vectors: Promises and Pitfalls," Expert Opin. Biol. Ther., 2015, 15(3):337-351.
Fernandes et al., "Bioprocess Development for Canine Adenovirus Type 2 Vectors," Gene Therapy, 2013, 20:353-360.
Hagner-Mcwhirter et al., "A Scalable Adenovirus Production Process, from Cell Culture to Purified Bulk," 2013, XP055591743, http://www.processdevelopmentforum.com/ppts/posters/27024 10061.pdf.
James et al., "Novel High-Throughput Approach for Purification of Infectious Virions," Sci. Reports, 2016, 6:36826 (11 pages), https://www.nature.com/articles/srep36826.
Kallel et al., "Large-Scale Adenovirus and Poxvirus-Vectored Vaccine Manufacturing to Enable Clinical Trials," Biotechnol J., 2015, 10:741-747.
Nestola et al., Rational Development of Two Flowthrough Purification Strategies for Adenovirus Type 5 and Retro Virus-Like Particles, Journal of Chromatograph A., 2015, 1426:91-101.
Shen et al., "Optimization and Scale-Up of Cell Culture and Purification Processes for Production of an Adenovirus-Vectored Tuberculosis Vaccine Candidate," Vaccine, 2016, 34(29):3381-3387.
IP.com Prior Art Database, 2013, "Simplified procedure during vaccine production", IPCOM000225002D, https://priorart.ip.com/IPCOM/000225002.
Lundgren et al., "Modernizing Legacy Vaccine Processes," Live Influenza virus production, 2015, https://www.dcvmn.org/IMG/pdf/vaccine_case_studies_mats_lundgre_g e_healthcare_.pdf, see Purification Workflow.

(Continued)

*Primary Examiner* — Nicole Kinsey White
*Assistant Examiner* — Ruixue Wang
(74) *Attorney, Agent, or Firm* — Eversheds-Sutherland (US) LLP

(57) ABSTRACT

The present invention relates to a method for virus purification. The present invention provides downstream processes for purification of adenovirus from cell culture harvest. More closely, it relates to a method for adenovirus purification using a virus capture and a virus polishing step.

7 Claims, 3 Drawing Sheets

(56) References Cited

OTHER PUBLICATIONS

Japanese Office Action for JP Application No. 2020-558871 mailed Feb. 13, 2023 (16 pages).
Chinese Office Action for CN Application No. 201980028038.0, mailed Jun. 27, 2023 (18 pages).
Second Chinese Office Action for CN Application No. 201980028038.0, mailed Apr. 12, 2024 (35 pages).

* cited by examiner

METHOD FOR ADENOVIRUS PURIFICATION

CROSS REFERENCE TO RELATED APPLICATIONS

This application claims the priority benefit of PCT/EP2019/060431 filed on Apr. 24, 2019, which claims priority to Great Britain Application No. 1806758.7 filed on Apr. 25, 2018, the entire contents of which are hereby incorporated by reference herein.

FIELD OF THE INVENTION

The present invention relates to a method for virus purification. The present invention provides downstream processes for purification of adenovirus from cell culture harvest. More closely, it relates to a method for adenovirus purification using a virus capture and a virus polishing step.

BACKGROUND OF THE INVENTION

Human adenoviruses have been classified into six species (A to F) with 55 known serotypes causing a wide range of illnesses, from mild respiratory infections in young children (known as the common cold) to life-threatening multi-organ disease in people with a weakened immune system. Adenoviruses are common pathogens that are widely used experimentally and in completed and ongoing clinical trials for gene delivery in oncology, cardioangiology, and regenerative medicine and as vaccine vectors.

Adenovirus is evaluated as vaccine delivery system in many preclinical and clinical studies of various infectious diseases (Kallel, H. and Kamen, A. A. Large-scale adenovirus and poxvirus-vectored vaccine manufacturing to enable clinical trials. *Biotechnol J* 10, 741-747 (2015). Adenovirus is also explored as a potential viral vector for gene therapy and as an oncolytic virus. To enhance productivity and to produce more effective and safer vaccines, several generations of recombinant adenovirus vectors have been developed (Appaiahgari, M. B. and Vrati, S. Adenoviruses as gene/vaccine delivery vectors: promises and pitfalls. *Expert Opin Biol Ther* 15, 337-351 (2015). The most studied adenovirus vector is the first generation of recombinant adenovirus serotype 5 (AdV5), making this a suitable system for development of a process for adenovirus production.

Chromatographic techniques are used for adenovirus purification but the results have often been insufficient in respect of purity, yield and capacity.

Thus, there is still a need to find better and more efficient ways for adenovirus purification, especially in those case the virus is to be used as adenoviral gene delivery vectors.

SUMMARY OF THE INVENTION

The present invention provides an efficient method for adenovirus purification with high capacity and high yield.

The invention relates to A method for adenovirus purification comprising the following steps: a) capturing adenovirus from an adenovirus-containing cell culture harvest on an anion exchanger resin; b) eluting said adenovirus with a shallow conductivity gradient with an increasing salt concentration of 15-25%, preferably 18-20%; c) adding said eluted adenovirus to a shell bead resin comprising a porous shell and a porous core, wherein the core is provided with hydrophobic interaction ligands and the shell is not provided with any ligands; and d) eluting said adenovirus from said shell bead resin in the flow through, wherein the adenovirus eluted in step d) comprises less than 1 ng/ml host cell protein (HCP).

Preferably the salt is NaCl and the gradient is increasing 18-20% and the salt concentration is 0-700 mM, such as 480-570 mM NaCl as in the Examples below or any interval between 0-700 mM that corresponds to a shallow gradient increasing 18-20% from the starting salt concentration.

Preferably the anion exchange resin is multimodal CAPTO™ Q ImpRes anion exchange resin and the shell bead resin is CAPTO™ Core 700 resin.

The anion exchange resin is packed in a column and the shell bead resin is packed in another column, and the eluted adenovirus is added (loaded) to the shell bead resin in a volume corresponding to 15-30 column volumes (CV), preferably 25-30 CV, of the column comprising shell bead resin. The porosity of the core and shell may be the same or different.

The adenovirus eluted in step d) is very pure and comprises no detectable impurities. The level of host cell protein (HCP) is undetectable or less than 1 ng/ml.

As shown in the experimental section, the recovery of the adenovirus eluted in step d) is 80-100%.

A preferred use of the adenovirus is as an adenoviral vector for cell therapy.

DETAILED DESCRIPTION OF THE INVENTION

Figure 1:
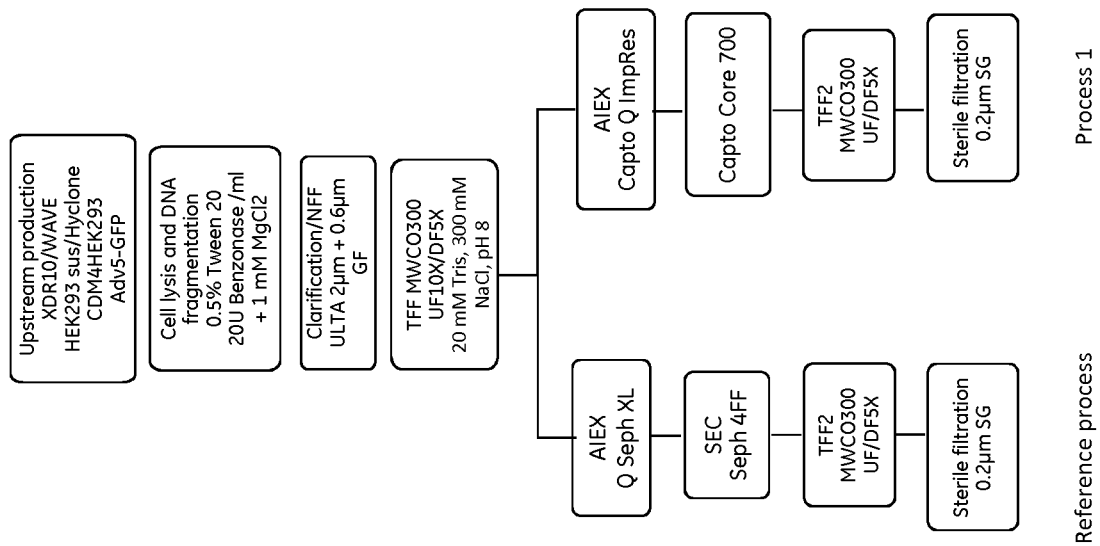
FIG. 1 shows an overview of two two-step chromatography processes for adenovirus purification, Process of the invention a Reference Process.

This invention describes the development of downstream chromatography steps for purification of adenovirus from HEK293 cell culture harvest. After screening of 10 different anion exchange or multimodal resins and 1 anion exchange membrane in small scale, two resins were selected based on highest dynamic binding capacity. Process conditions were optimized and polishing steps were included for further reduction of impurities to meet regulatory requirements. The performance was compared in small scale for a first anion exchange capture step followed by a polishing by either size exclusion or by using CAPTO™ core multimodal resin. A reference process and the developed downstream Process of the invention were compared in larger scale, using 3 L cell culture harvest. Although the overall process outcome shows a comparable performance between the developed two-step chromatography processes, the load capacity was approximately 150-fold higher for the polishing step of the inventive process by the use of CAPTO™ core 700 resin instead of traditional size exclusion.

Materials and Methods

Virus Propagation and Sample Preparation

HEK293.2sus cells (ATCC), grown in HyClone™ CDM4HEK medium in the Xcellerex™ XDR-10 or ReadyToProcess WAVE™ 25 bioreactor system, were infected with AdV5 coding for green fluorescent protein (GFP). The cells were lysed in the bioreactor with 0.5% Tween™ 20 during mixing for 4 h. Simultaneously, 20 U/mL Benzonase™ was added to digest host cell DNA (hcDNA). Clarification of the harvest material was performed by normal flow filtration (NFF), using a combination of ULTA™ 2 µm and 0.6 µm GF filters for removal of cell debris and for an initial impurity reduction. Tangential flow filtration (TFF) was conducted on ÄKTA™ flux 6 filtration system, using a hollow fiber filter with a nominal molecular weight cut-off of $M_r$ 300 000 for concentration and buffer exchange to 20 mM Tris, pH 8.0. Sodium chloride was used for sample conditioning prior to the capture step.

Development of Adenovirus Capture Step

Screening of dynamic binding capacity (DBC) was performed in 1 mL prepacked HiTrap™ columns for the resins (RESOURCE™ Q column for the SOURCE Q 15) and in a 1 mL ReadyToProcess Adsorber Q capsule for the membrane, using the ÄKTA pure 25 chromatography system. DBC was determined at different NaCl concentrations in 20 mM Tris, pH 8.0 (Table 1). Load of sample subjected to TFF was performed at a residence time of 10 min for the column and 0.2 min for the capsule, until breakthrough of virus.

Optimization of Elution Conditions

Based on the results from the DBC screening, CAPTO™ Q, CAPTO™ Q ImpRes, Q Sepharose XL, SOURCE 15Q, and CAPTO™ adhere ImpRes resins as well as the ReadyToProcess Adsorber Q membrane were selected for further evaluation. Linear elution gradient was evaluated in 1 mL prepacked columns for the selected resins, and for the membrane, a 1 mL membrane capsule was used. The columns and capsule were equilibrated with 20 mM Tris, pH 8.0+300 mM NaCl (0 mM NaCl for CAPTO™ adhere ImpRes). Sample load was performed at 80% of DBC. Fractions were collected for analysis throughout the elution gradient up to 700 mM NaCl.

CAPTO™ Q, CAPTO™ Q ImpRes, and ReadyToProcess Adsorber Q were selected for further optimization, and step elution conditions were evaluated for these adsorbents. After the load step, a wash step with as high NaCl as possible without breakthrough of virus, followed by a step for complete virus elution at an as low increase in conductivity as possible, was desired to avoid coelution of DNA with the virus. The performance of ReadyToProcess Adsorber Q was evaluated with samples subjected to NFF only or to NFF followed by TFF.

Resin Evaluation for Adenovirus Polishing Step

CAPTO™ Core 700 (prepacked in 1 mL HiTrap column) and Sepharose 4 Fast Flow (packed in HiScale™ 16/40, 71 mL column volume [CV]) resins were evaluated for the polishing step. Material purified in the evaluated capture steps, using CAPTO™ Q, CAPTO™ Q ImpRes, and ReadyToProcess Adsorber Q, was used as sample. Ten percent of the CV was loaded on Sepharose Fast Flow and up to 30 CV was loaded onto CAPTO™ Core 700. To determine largest possible sample load volume at accepted virus purity for CAPTO™ Core 700, fractions were collected throughout the sample load phase and analyzed for impurity content.

All resins were from GE Healthcare Bio-Sciences AB.

Scale-Up of Adenovirus Capture and Polishing Steps

Two processes-Process 1 (=Process of the invention) using samples subjected to TFF and a combination of CAPTO™ Q ImpRes anion exchange resin and CAPTO™ Core 700 resin; and a reference process using samples subjected to TFF and a combination of Sepharose QXL anion exchange and Sepharose 4 Fast Flow size exclusion chromatography (SEC) resin-were scaled up for processing of 3 L cell culture harvest. For capture, CAPTO™ Q ImpRes was packed in a HiScale 26 column (88 mL), whereas Sepharose QXL packed in HiScale 50 (249 mL). For polishing, CAPTO™ Core 700 was packed in a HiScale 16 column (10 mL) and Sepharose 4 Fast Flow was packed in a HiScale 50 column (382 mL). Columns were operated on the ÄKTA pure 150 system. After the polishing step, a second TFF step was included for concentration, formulation, and final sterile filtration. Processes were performed in duplicate.

Analytical Methods

Total virus titer was analyzed in triplicate samples by qPCR using PureLink™ Viral RNA/DNA Mini Kit, TaqMan™ Universal PCR Master mix, and forward and reverse primers for hexon DNA and TaqMan MGB 6-FAM probe on the StepOnePlus™ Real-Time PCR System (all Applied Biosystems). Human AdV5 DNA ($3.1 \times 10^7$ copies/mL) (ViraPur) was used as standard.

Infectious virus titer was analyzed in triplicate samples by automated fluorescence microscopy of live cells using the IN Cell Analyzer, and the images were analyzed for GFP signal (coded by virus) with a methodology similar to $TCID_{50}$.

A HPLC method was used for analysis of intact virus particles, using a 1 mL Tricorn™ 5/50 column packed with Q Sepharose XL. Elution was performed with a gradient of NaCl in 20 mM Tris, pH 7.5 at a flow rate of 1.5 mL/min.

A BCA assay kit (Thermo Scientific) with an albumin standard was used for analysis of total protein concentration, and total DNA was determined with Quant-iT™ PicoGreen™ dsDNA Reagent (Invitrogen). Analyses were performed in duplicate.

Concentration of host cell protein (HCP) was determined with a HEK293 HCP ELISA kit (Cygnus).

Concentration of hcDNA was determined in triplicate samples by qPCR (reagents from Applied Biosystems), using primers for GAPDH (Invitrogen) and purified HEK293 DNA as standard. Samples were prepared using PrepSEQ™ Residual DNA Sample Preparation kit and MagMax™ Express 96 purification instrument (Life Technologies).

Experimental Part

Experiment 1: Adenovirus Capture Step

A comprehensive screening of anion exchange and multimodal chromatography adsorbents was conducted. Screening was conducted in 1 mL HiTrap columns, which provided sufficient sample volume for detection of the virus with available methods. As shown below, the membrane as well as resins based on a smaller bead size, and thereby larger surface area for virus binding, offered the highest capacity (Table 1).

TABLE 1

| | DBC indicated as virus particles (vp)/mL resin | | | | | | | |
|---|---|---|---|---|---|---|---|---|
| | 0 mM | | | NaCl | | | | |
| | NaCl | 100 mM | 200 mM | 300 mM | 350 mM | 400 mM | 450 mM | 480 mM |
| CAPTO™ Q | $1.51 \times 10^{11}$ | | $2.32 \times 10^{11}$ | $3.78 \times 10^{11}$* | $3.78 \times 10^{11}$* | $3.78 \times 10^{11}$* | | |
| CAPTO™ Q ImpRes | $1.81 \times 10^{11}$ | $2.01 \times 10^{11}$ | $2.12 \times 10^{11}$ | $3.75 \times 10^{11}$* | $5.63 \times 10^{11}$* | $7.04 \times 10^{11}$* | $7.04 \times 10^{11}$* | $6.57 \times 10^{11}$* |

TABLE 1-continued

| | DBC indicated as virus particles (vp)/mL resin | | | | | | | |
|---|---|---|---|---|---|---|---|---|
| | 0 mM | | | NaCl | | | | |
| | NaCl | 100 mM | 200 mM | 300 mM | 350 mM | 400 mM | 450 mM | 480 mM |
| CAPTO™ adhere | $1.61 \times 10^{11}$ | $1.61 \times 10^{11}$ | $1.31 \times 10^{11}$ | | | | | |
| CAPTO™ adhere ImpRes | $2.22 \times 10^{11}$ | $2.22 \times 10^{11}$ | $2.01 \times 10^{11}$ | $2.12 \times 10^{11}$ | | | | |
| CAPTO™ DEAE | $1.21 \times 10^{11}$ | | | $3.02 \times 10^{10}$ | | | | |
| Q Sepharose Fast Flow | | $9.07 \times 10^{10}$ | $1.01 \times 10^{11}$ | | | | | |
| Q Sepharose XL | $1.21 \times 10^{11}$ | | $2.22 \times 10^{11}$ | $2.01 \times 10^{11}$ | | | | |
| DEAE Sepharose FF | $1.31 \times 10^{11}$ | | $9.07 \times 10^{11}$ | | | | | |
| ANX Sepharose FF | $1.11 \times 10^{11}$ | | $1.11 \times 10^{11}$ | | | | | |
| Q Sepharose Fast Flow | | | | $1.11 \times 10^{12}$ | | | | |
| ReadyToProcess Adsorber Q nano, 1 mL | | | | $1.71 \times 10^{11}$ | | | | |

*DBC was determined with sample from a different preparation.

In linear elution gradient experiments, CAPTO™ Q ImpRes and CAPTO™ Q provided good separation of adenovirus from impurities and were thus selected for further evaluation (not shown). Although ReadyToProcess Adsorber Q provided insufficient virus purity using a linear elution gradient (not shown), the membrane was also selected for further evaluation due to its high binding capacity.

As it was discovered during process optimization that the required conductivity for complete elution of virus was significantly higher in step elution gradient compared with linear elution gradient for both CAPTO™ Q and CAPTO™ Q ImpRes (not shown), linear elution gradient was selected for the resins because the higher the elution conductivity for the virus, the higher the risk of coelution of the virus with DNA. DNA is negatively charged and binds strongly to anion exchangers, and longer DNA sequences (e.g., incomplete fragmented DNA after Benzonase treatment) binds stronger than shorter DNA fragments. Lower elution conductivity resulted in reduced hcDNA in the virus elution pool.

Experiment 2: Adenovirus Polishing Step

An adenovirus polishing step was included in the purification process to further reduce impurities. For this step, both CAPTO™ Core 700 multimodal and Sepharose 4 Fast Flow SEC resins were evaluated. CAPTO™ Core 700 consists of an inert shell and a ligand-containing core, providing dual functionality to the resin. Pores in the shell allow small proteins and impurities to enter and be captured in the core, while the virus particles pass in the flow-through.

Adenovirus recovery and purity were analyzed over the process steps. Sepharose 4 Fast Flow and CAPTO™ Core 700 resins offered a similar performance in terms of adenovirus purity, however, CAPTO™ Core 700 exhibited a clear advantage over Sepharose 4 Fast Flow in terms of sample load volume. Sample load for CAPTO™ Core 700 was up to 30 CV, whereas only 0.1 CV was loaded onto the Sepharose 4 Fast Flow column. Virus recovery was also determined to be higher for CAPTO™ Core 700, although high variability of the qPCR assay. The overall downstream process results for the smaller scale are summarized in Table 3.

TABLE 3

Results from adenovirus polishing steps

| Capture | Polishing | Load | Recovery of total virus particles (%)* | Total protein (µg/dose) | Total DNA (ng/dose) | hcDNA (ng/dose) |
|---|---|---|---|---|---|---|
| CAPTO™ Q ImpRes | Sepharose 4 Fast Flow | 0.1 CV | 39/57 | <LOD | <LOD | <LOD |
| | CAPTO™ Core 700 | 26 CV | 65/100 | <LOD | <LOD | <LOD |
| CAPTO™ Q | Sepharose 4 Fast Flow | 0.1 CV | 57 | <LOD | <LOD | <LOD |
| | CAPTO™ Core 700 | 18 CV | 100/100 | <LOD | <LOD | <LOD |

*Total virus titer monitored by qPCR.
Two numbers indicate that the same sample was analyzed twice.
LOD = 1 ng/ml Although CAPTO™ Q provided higher impurity reduction than CAPTO™ Q ImpRes, the results from evaluation of polishing resins show that CAPTO™ Core 700 reduced the remaining impurities in eluates from both resins to below limit of detection (LOD). As CAPTO™ Q ImpRes provided higher load capacity, supporting process economy improvements, CAPTO™ Q ImpRes was selected over CAPTO™ Q.

Based on these results, two parallel processes were compared: Process 1 combining CAPTO™ Q ImpRes and CAPTO™ Core 700, and Reference combining Sepharose QXL and Sepharose 4 Fast Flow (FIG. 1).

Experiment 3: Scale-Up Adenovirus Purification Process

Processes 1 and Reference process were scaled for purification of adenovirus from 3 L cell culture harvest. Process 1 showed a clear advantage over Reference process in terms of impurity reduction, and yield over the polishing step, but the overall results for the scaled-up experiments provided comparable results between the processes. In the scaled-up experiments, hcDNA levels in the final samples were similar.

However, Process 1 reduced HCP levels to below LOD, whereas in Reference process, HCP levels in the final sample were 22 ng/ml in average. The amount of total virus particles in the final samples was comparable between the processes (Process 1: $4.9 \times 10^{13}$ and $5.3 \times 10^{13}$ vp; Reference process: $3.4 \times 10^{13}$ and $5.1 \times 10^{13}$ vp).

Figure 2:
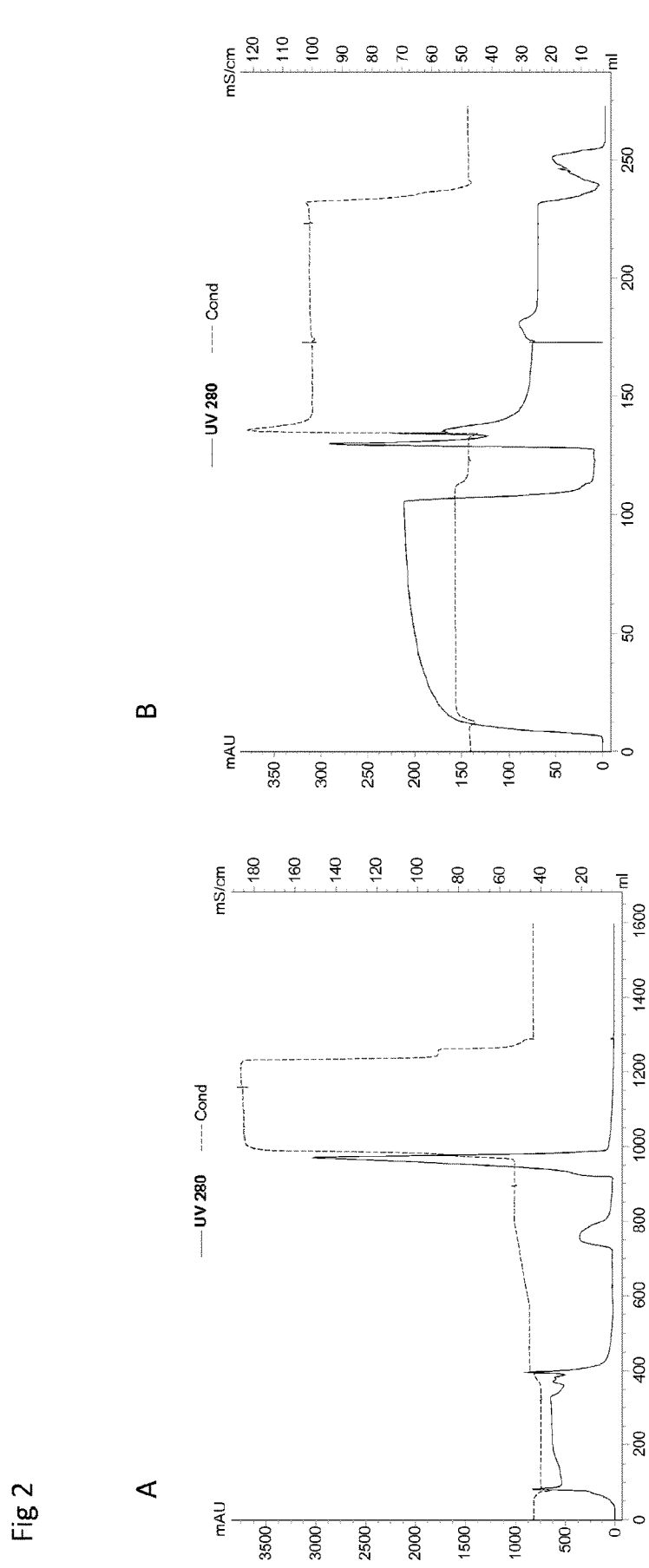
FIG. 2 shows chromatograms from scale-up the Process of the invention, using (A) CAPTO™ Q ImpRes for the capture step and (B) CAPTO™ Core 700 for the polishing step.
Figure 3:
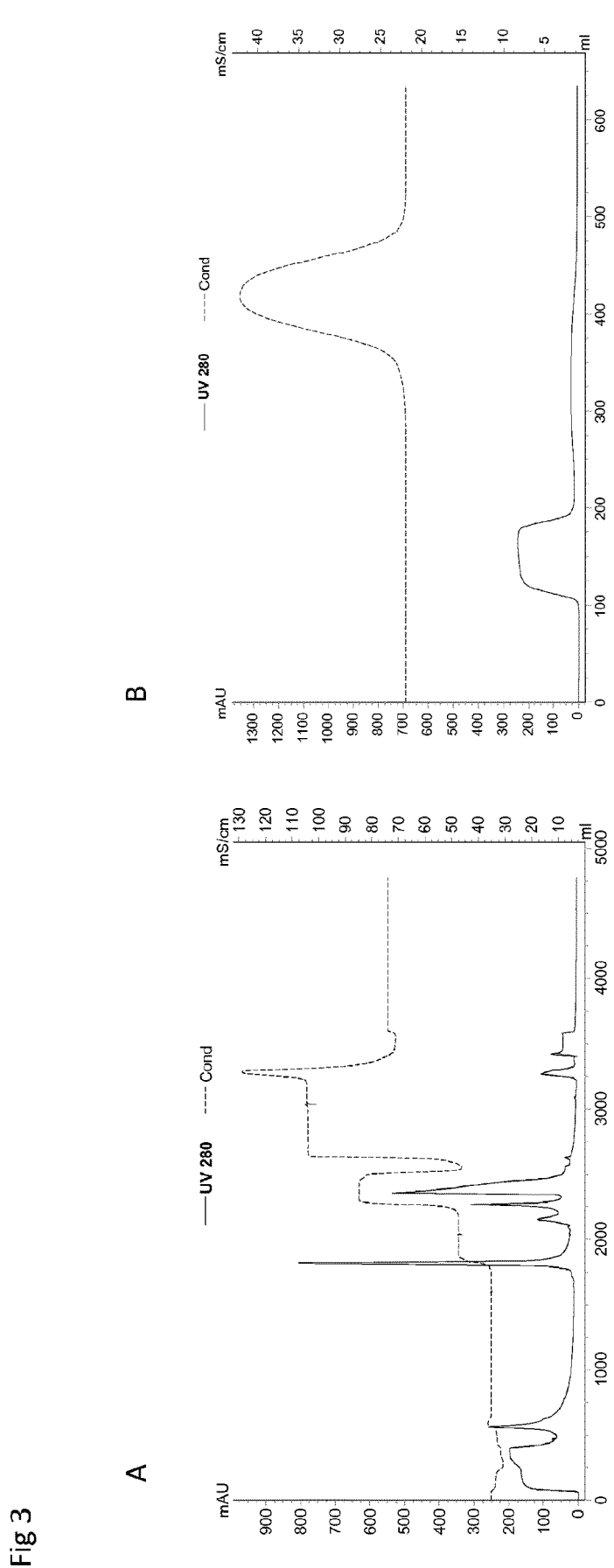
FIG. 3 shows chromatograms for the Reference process, using A) Sepharose QXL for the capture step and (B) Sepharose 4 Fast Flow for the polishing step.

Chromatograms for Process 1 are shown in FIG. 2 and for reference process in FIG. 3. Results from the scaled-up processes are summarized in Table 4.

Process 1 (FIG. 2A)
 Sample: Harvest subjected to NFF and TFF in 20 mM Tris, pH 8.0+450 mM NaCl
 Resin: CAPTO™ Q ImpRes
 Column: HiScale 26
 Load: $5.6 \times 10^{11}$ VP/mL resin (80% of QB10, 10 min residence time)
 Binding buffer: 20 mM Tris, pH 8.0+450 mM NaCl, 2 mM MgCl$_2$
 Wash: 2 CV 20 mM Tris, pH 8.0+480 mM NaCl, 2 mM MgCl$_2$
 Elution buffer: 20 mM Tris, pH 8.0+450 to 570 mM NaCl in 2.5 CV, 2 mM MgCl$_2$
 System: ÄKTA™ pure 150
Process 1 (FIG. 2B)
 Sample: Eluate from capture step
 Resin: CAPTO™ Core 700
 Column: HiScale 16
 Load: 9 CV CAPTO™ Q ImpRes eluate
 Buffer: 20 mM Tris, pH 8.0+500 mM NaCl, 2 mM MgCl$_2$
 Wash: 1.5 CV of binding buffer
 System: ÄKTA pure 150
Reference Process (FIG. 3A)
 Sample: Harvest subjected to NFF and TFF in 20 mM Tris, pH 8.0+350 mM NaCl
 Resin: Q Sepharose XL
 Column: HiScale 50
 Load: $8.9 \times 10^{11}$ VP/mL resin (80% of QB10, 10 min residence time)
 Binding buffer: 20 mM NaP, pH 7.3+350 mM NaCl, 2 mM MgCl$_2$, 2% sucrose
 Wash: 5 CV of 20 mM NaP, pH 7.3, 350 mM NaCl, 2 mM MgCl$_2$, 2% sucrose
 Elution buffer: 20 mM NaP, pH 7.3+500 mM NaCl, 2 mM MgCl$_2$, 2% sucrose
 System: ÄKTA pure 150
Reference Process (FIG. 3B)
 Sample: Eluate from capture step
 Load: 0.2 CV Q Sepharose XL eluateResin: Sepharose 4 Fast Flow
 Column: HiScale 50
 Load: 0.2 CV
 Buffer: 20 mM sodium phosphate, pH 7.3+200 mM NaCl, 2 mM MgCl$_2$, 2% sucrose
 Wash: 1.5 CV of binding buffer
 System: ÄKTA pure 150

TABLE 4

Adenovirus recovery and purity in Process of the invention (Process 1) and Reference process

| Process variant | Recovery TVP % | Recovery IVP % | HCP ng/ml | Total protein µg/dose | gDNA ng/dose | Total DNA ng/dose |
|---|---|---|---|---|---|---|
| Reference run 1 | 31/38 | 36 | 17 | 11/13 | <LOD | 6/8 |
| Reference run 2 | 35/64 | 53 | 27 | 38/20 | 3 | 13/10 |
| Reference average | 42 | 45 | 22 | 20 | <LOD - 3 | 9 |
| Process 1 run 1 | 46/68 | 39 | <LOD | 13/11 | <LOD | 4/12 |
| Process 1 run 2* | 17 | 40 | <LOD | 10 | <LOD | 20 |
| Process 1 average | 37 | 40 | <LOD | 11 | < LOD | 14 |

*Analysis only performed once.
Two numbers indicate that the same sample was analyzed twice.
LOD = 1 ng/ml A CAPTO™ Impres shallow salt gradient from 480 mM to 570 mM NaCl was critical to separate DNA fragments from virus particles. This corresponds to a 19% increase in salt concentration over the gradient or 7.5% increase in salt concentration per CV in the gradient (gradient calculation: 90 mM change over 2.5 CV, 36 mM/CV). The polishing with CAPTO™ Core 700 as a second step resulted in a final bulk with a significant reduction in debris or impurities by Transmission electron microscopy (TEM) imaging compared to a reference process (Sepharose Q XL step elution followed by size exclusion, FIGS. 3A and B, Table 4). The procedure is expected to perform equally well with a gradient of KCl or LiCl, or any combination of NaCl, KCl and LiCl.

From the above it clearly appears that Process 1 using a combination of CAPTO™ Q ImpRes anion exchange resin and CAPTO™ Core 700 resin has several advantages over the Reference process.

In smaller scale, Process 1 showed a clear advantage with regard to impurity reduction. In the scale-up experiments, Process 1 showed better HCP reduction (<LOD vs 22 ng/ml). This and other features makes the method of the invention a suitable method for purification adenoviral vectors for cell therapy.

Another major benefit of the invention was that up to 30 column volumes (CV) could be loaded the CAPTO™ Core 700 column in Process 1 whereas only 0.2 CV could be loaded in Reference process (150-fold higher load capacity). Furthermore, the yield was clearly better for polishing in Process 1 using the shell bead step compared to size exclusion chromatography, SEC (Table 3).

The invention claimed is:

1. A method for adenovirus purification comprising the following steps: a) capturing adenovirus from an adenovirus-containing cell culture harvest on an anion exchanger resin, wherein the anion exchange resin comprises an agarose base matrix modified with a quaternary ammonium strong ion exchange ligand; b) eluting said adenovirus with a shallow conductivity gradient with an increasing salt concentration (mM) of 15-25% over the gradient; c) adding said eluted adenovirus to a shell bead resin comprising a porous, inert shell and a porous core, wherein the core is provided with hydrophobic interaction ligands; and d) eluting said adenovirus from said shell bead resin in the flow through, wherein the adenovirus eluted in step d) comprises less than 1 ng/ml host cell protein (HCP).

2. The method according to claim 1, wherein the salt is selected from NaCl, KCl and LiCl, or any combinations thereof.

3. The method according to claim 1, wherein the salt is NaCl and the gradient is increasing 18-20% and the salt concentration is between 0-700 mM.

4. The method according to claim 1, wherein the anion exchange resin is packed in a column and the shell bead resin is packed in another column, and wherein the adenovirus eluted from the anion exchanger resin is added to the shell bead resin in a volume corresponding to 15-30 column volumes (CV) of the column comprising shell bead resin.

5. The method according to claim 4, wherein the adenovirus eluted from the anion exchanger resin is added to the shell bead resin in a volume corresponding to 25-30 column volumes (CV) of the column comprising shell bead resin.

6. The method according to claim 1, wherein the porosity of the core and shell is the same of the shell bead resin.

7. The method according to claim 1, wherein the porosity of the core and shell is different of the shell bead resin.

* * * * *